(12) United States Patent
Kuetting et al.

(10) Patent No.: US 12,138,156 B2
(45) Date of Patent: Nov. 12, 2024

(54) PROSTHETIC HEART VALVE

(71) Applicant: NVT AG, Morges (CH)

(72) Inventors: Maximilian Kuetting, Boeblingen (DE); Natalia Kalugin, Balingen (DE); Erika Balsamo, Duesseldorf (DE); Marcos Centola, Hechingen (DE)

(73) Assignee: NVT AG, Morges (CH)

( * ) Notice: Subject to any disclaimer, the term of this patent is extended or adjusted under 35 U.S.C. 154(b) by 716 days.

(21) Appl. No.: 17/238,433

(22) Filed: Apr. 23, 2021

(65) Prior Publication Data

US 2021/0236282 A1 Aug. 5, 2021

Related U.S. Application Data

(63) Continuation of application No. PCT/EP2019/079043, filed on Oct. 24, 2019.

(30) Foreign Application Priority Data

Oct. 26, 2018 (DE) ..................... 10 2018 126 828.9

(51) Int. Cl.
*A61F 2/24* (2006.01)
*A61L 27/16* (2006.01)
(Continued)

(52) U.S. Cl.
CPC ............ *A61F 2/2418* (2013.01); *A61L 27/16* (2013.01); *A61L 27/18* (2013.01); *A61L 27/3625* (2013.01);
(Continued)

(58) Field of Classification Search
CPC .......... A61F 2/2418; A61F 2250/0069; A61L 27/16; A61L 27/18; A61L 27/3625; A61L 2430/20
See application file for complete search history.

(56) References Cited

U.S. PATENT DOCUMENTS 9,668,856 B2 * 6/2017 Para ...................... A61F 2/2418
10,080,652 B2 9/2018 Backus et al.
(Continued)

FOREIGN PATENT DOCUMENTS

EP 1967163 A2 9/2008
JP 2014-531292 A 11/2014
(Continued)

OTHER PUBLICATIONS

International Preliminary Report on Patentability for International Application No. PCT/EP2019/079043, mailed May 6, 2021.
(Continued)

*Primary Examiner* — Suzette J Gherbi
(74) *Attorney, Agent, or Firm* — Jason H. Vick; Womble Bond Dickinson (US) LLP

(57) ABSTRACT

The present invention concerns a prosthetic heart valve for supporting or replacing a non- or malfunctioning native heart valve, the prosthetic heart valve comprising an expandable generally tubular stent support, having an inner surface and an outer surface, and comprising a valve element, having an outer surface, an inner surface, and comprising a plurality of sealing elements, wherein the sealing elements are—spaced apart from one another—circumferentially attached to the outer surface of the valve element and form a lip-shaped element radially protruding from the outer surface of the valve element, wherein the valve element is mounted on the inner surface of the stent support.

13 Claims, 3 Drawing Sheets

(51) Int. Cl.
  *A61L 27/18* (2006.01)
  *A61L 27/36* (2006.01)
(52) U.S. Cl.
  CPC ... *A61F 2250/0069* (2013.01); *A61L 2430/20* (2013.01)

(56) References Cited

U.S. PATENT DOCUMENTS

| | | | | |
|---|---|---|---|---|
| 10,751,172 | B2* | 8/2020 | Para | A61F 2/2418 |
| 2006/0004439 | A1* | 1/2006 | Spenser | A61F 2/2436 |
| | | | | 623/2.11 |
| 2006/0004442 | A1* | 1/2006 | Spenser | A61F 2/2472 |
| | | | | 623/1.21 |
| 2009/0281618 | A1* | 11/2009 | Hill | A61F 2/2457 |
| | | | | 623/1.26 |
| 2011/0098800 | A1* | 4/2011 | Braido | A61F 2/2418 |
| | | | | 623/1.26 |
| 2011/0098802 | A1* | 4/2011 | Braido | A61F 2/2412 |
| | | | | 623/2.11 |
| 2013/0018458 | A1* | 1/2013 | Yohanan | A61F 2/2436 |
| | | | | 623/2.38 |
| 2013/0090729 | A1 | 4/2013 | Gregg et al. | |
| 2013/0197622 | A1* | 8/2013 | Mitra | A61F 2/2418 |
| | | | | 623/1.15 |
| 2014/0277417 | A1 | 9/2014 | Schraut et al. | |
| 2015/0005863 | A1* | 1/2015 | Para | A61F 2/2418 |
| | | | | 623/1.2 |
| 2017/0189174 | A1* | 7/2017 | Braido | A61F 2/2436 |
| 2017/0224482 | A1* | 8/2017 | Para | A61F 2/2418 |
| 2019/0053895 | A1* | 2/2019 | Levi | A61F 2/2415 |
| 2022/0395368 | A1* | 12/2022 | Braido | A61F 2/2403 |
| 2023/0372093 | A1* | 11/2023 | Bukin | A61F 2/2418 |

FOREIGN PATENT DOCUMENTS

| | | |
|---|---|---|
| JP | 2016-509891 A | 4/2016 |
| WO | WO 2014/139545 A1 | 9/2014 |
| WO | WO 2018/170149 | 9/2018 |

OTHER PUBLICATIONS

International Search Report for International Application No. PCT/EP2019/079043, mailed Feb. 7, 2020.

Written Opinion for International Application No. PCT/EP2019/079043, mailed Feb. 7, 2020.

Notice of Reason for Refusal (Including Translation) for corresponding Japanese Patent Application No. 2021-523044, mailed Jun. 14, 2022.

* cited by examiner

PROSTHETIC HEART VALVE

CROSS REFERENCES TO RELATED APPLICATIONS

This application is a continuation of international patent application PCT/EP2019/079043, filed on Oct. 24, 2019, designating the U.S., which international patent application has been published in English language and claims priority from German patent application 10 2018 126 828.9, filed on Oct. 26, 2018. The entire contents of these priority applications are incorporated herein by reference.

The present invention relates to a prosthetic heart valve for supporting or replacing a non- or malfunctioning native heart valve.

BACKGROUND

Heart valve replacement is necessary where the native heart valve is damaged, mal- or nonfunctioning. In the heart, cardiac valves maintain the unidirectional flow of blood by opening and closing depending on the difference in pressure on each side. The mammalian heart comprises four chambers, i.e. two atria, which are the filling chambers, and two ventricles, which are the pumping chambers. In a mammalian heart, there are four heart valves present which normally allow blood to flow in only one direction through the heart, whereby a heart valve opens or closes depending on the differential blood pressure on each side.

The four main valves in the heart are the mitral valve, representing a bicuspid valve, and the tricuspid valve, which are between the upper atria and the lower ventricles, respectively, and thus are called atrioventricular (AV) valves. Further, there are the aortic valve and the pulmonary valve which are in the arteries leaving the heart. The mitral valve and the aortic valve are in the left heart and the tricuspid valve and the pulmonary valve are in the right heart.

The valves incorporate leaflets or cusps, wherein each valve has three cusps, except for the mitral valve, which only has two.

Ideally, native leaflets of a heart valve move apart from each other when the valve is in an open position, and meet or "coapt" when the valve is in a closed position. As such, a heart valve can be affected by a range of diseases and can, therefore, require cardiac valve replacement. The valve can either become leaky, i.e. regurgitant or insufficient, in which case the aortic valve is incompetent and blood flows passively back to the heart in the wrong direction. Further, the valve can become partially shut, i.e. stenotic, in which case the valve fails to open fully, thereby obstructing blood flow out from the heart. The two conditions frequently co-exist.

Heart valve replacement traditionally requires median sternotomy and thus open heart surgery, which is a major impact on the patient to be treated: The sternum is sawed in half and after opening of the pericardium, the patient is placed on a cardiopulmonary bypass machine. Once the patient is on bypass, the patient's diseased aortic valve is removed and a mechanical or tissue valve is put in its place. Besides the physical stress associated with this operation, there is a risk of death or serious complications from open heart surgery, in particular depending on the health and age of the patient.

However, systems have been developed which allow percutaneous introduction and deployment of prosthetic heart valves, by means of which open heart surgeries can be avoided. The desire for less invasive approaches is linked with the fact that a significant proportion of patients, especially elderly persons or those with significant comorbidities or severe left ventricular dysfunction, are not referred for (open heart) surgery. The deployment of such heart valve prostheses can either be achieved retrograde, i.e. against normal blood flow, or antegrade, with blood flow. The prosthetic heart valve can be reduced in diameter, e.g., by crimping onto a balloon catheter or by being contained within a sheath component of a delivery catheter keeping it in a compressed state, and advanced through the venous or arterial vasculature. Once the prosthetic valve is positioned at the site to be treated, e.g. within an impaired or non-functioning native valve, the stent structure of the prosthetic heart valve may be expanded, e.g. via balloon expansion or by using a self-expanding stent-support material to hold the prosthetic valve firmly in place.

For percutaneous valve replacements, various types and configurations of prosthetic heart valves are presently used, wherein the actual shape and configuration of any particular prosthetic heart valve is dependent, on the one hand, upon the valve being replaced. Generally, the prosthetic heart valve designs attempt to replicate the function of the valve being replaced and thus will regularly include valve leaflet-like structures used with either bioprosthesis, which are usually made from animal tissues, either animal heart valve tissue or animal pericardial tissue, and which are treated to prevent rejection and to prevent calcification, or mechanical heart valve prostheses, which are generally composed entirely of synthetic or non-biological materials. As such, the replacement valves may include a valved segment that is mounted in some manner within an (self-)expandable stent structure. There are two types of stents on which the valves structures are ordinarily mounted: self-expanding stents and balloon-expandable stents. To place such valves into a delivery apparatus and ultimately into a patient, the valve must first be collapsed or crimped to reduce its circumferential size.

When a collapsed prosthetic valve has reached the desired implant site in the patient, i.e. at or near the annulus of the patient's heart valve that is to be replaced by the prosthetic valve, the prosthetic valve is deployed or released from the delivery apparatus and expanded to full operating size. With balloon-expandable valves, generally the entire valve is released and subsequently expanded by an expandable balloon positioned within the valve stent. With self-expanding valves, the deployment systems regularly comprise a retractable sheath, upon withdrawing of which the stent automatically begins to expand.

For a fully functioning prosthetic heart valve it is crucial that all of its components fulfill their respective task: The valve, on the one hand, needs to be adequately attached to the stent support, since otherwise the valve is prone to failure, and valve failure, in the circulatory system, has significant consequences for the patient. On the other hand, the stent support needs to fully expand and, thus, guarantee the secure fixation within the heart vessels.

Also, a proper fixation of the prosthetic heart valve replacing the native diseased heart valve very often is complicated due to, e.g., calcification of the native valve. The calcified valve-tissue renders irregular the annular ring, making it difficult to securely fixate the prosthetic replacement valve in the annular ring.

Further, the loading of the valve onto a deployment system for minimally invasive procedures can be quite challenging, since the heart valve prosthesis-due to its nature-needs to be carefully loaded while at the same time its compression is mandatory for getting it tightly packed onto the deployment system.

Although transcatheter delivery methods have provided safer and less invasive methods for replacing a defective native heart valve, leakage between the implanted prosthetic heart valve and the surrounding native tissue still is a recurring problem. Leakage sometimes occurs due to the fact that minimally invasive and percutaneous replacement of cardiac valves typically does not involve actual physical removal of the diseased or impaired heart valve. Rather, the replacement stented prosthetic heart valve is delivered in a compressed state to the valve site, where it is expanded to its operational state within the valve to be treated. Through the radial force of the prosthetic heart valve's stent-support, the impaired native leaflets are pressed to the side walls. Since often the leaflets of the impaired native valve prevent the stent support to complete conform with the native valve, paravalvular leakage (PVL) is a frequent consequence, which causes blood to leak through the gaps between the implanted prosthetic heart valve and the impaired native valve due to significant pressure gradients across the valve.

In view of the above, there is a constant need for improving the deployment and fixation of prosthetic heart valves in the heart to be treated, while simultaneously guaranteeing an easy loading onto a delivery system and a smooth release of the prosthetic heart valve in the heart vessel from the deployment system.

Thus, it is an object of the present invention to provide for a prosthetic heart valve that fulfills the requirements above and overcomes the drawbacks of the presently available heart valve prostheses.

SUMMARY OF THE INVENTION

According the invention, this and other objects are solved by a prosthetic heart valve, the prosthetic heart valve being expandable from a compressed state to an expanded state, and comprising an expandable generally tubular stent support, and having a proximal end, a distal end, and a longitudinal axis extending from the proximal end to the distal end, wherein the tubular stent support has an inner surface and an outer surface, a valve element, having an outer surface, an inner surface, leaflets, a longitudinal axis and a circumference; a plurality of sealing elements, wherein the sealing elements are—spaced apart from one another-circumferentially attached to the outer surface of the valve element without being tangent to one another, such, that each of sealing element, in the expanded state, forms a lip-shaped element radially protruding from the outer surface of the valve element; further, the valve element having the sealing elements attached thereon is mounted on the inner surface of the stent support.

With the prosthetic heart valve of the invention, or rather due to the specific design, i.e. with the sealing elements being attached on the outer surface of the valve element and with the valve element being mounted onto the inner surface of the stent support, a convenient transcatheter prosthetic heart valve is provided allowing a tight compression on its deployment system while at the same time guaranteeing a good sealing of gaps between the prosthetic heart valve and the native impaired, diseased or non-/malfunctioning valve tissue.

A "lip-shaped element" as presently claimed and disclosed is meant to comprise any shape of a, preferably flat sealing element, that is folded, preferably in its middle, or is otherwise shaped to have this configuration, such, that the folded or otherwise formed shape forms two flat elements lying above each other but which are generally freely movable with respect to one another, while the shape is attached-via a portion that is shared by the two elements—to the valve element. In other words, the sealing elements are attached to the valve to have pairwise flaps attached to the valve element, each pair forming a "lip portion".

Also, according the invention, the sealing elements are spaced apart from one another and do not touch each other, and, thus, are not "tangent" to one another. The sealing elements, thus, are distributed over the circumference of the valve element.

In the prosthetic heart valve of the invention, the provision and arrangement of a lip-shape of the sealing elements, allows an enlargement of their outer surface/external surface.

Also, with the special shape of the sealing elements protruding from the valve element's outer surface and at least partially through open structures of the stent support, a better and tighter anchoring of the prosthetic heart valve within the location to be treated can be achieved, and, thus, a unwanted migration of the prosthetic heart valve is avoided. This is particularly due to the fact that the lip-shaped sealing elements, which protrude through the open structures of the stent support or stent frame, together with the stent support/frame increase the friction of the prosthetic heart valve relative to the walls of the vessel the prosthetic heart valve is implanted in. As a consequence, the radial forces exerted by the self-expanding stent support/frame are improved. Further, due to the specific construction of the prosthetic heart valve of the invention, and particularly due to the sealing elements, the overall stability and grip of the prosthetic heart valve is increased, which is a prerequisite in its implanted position for having the prosthetic heart valve performing its intended proper function.

Thus, with the prosthetic heart valve of the invention, and particularly the specific design of the sealing elements, a better anchoring in, e.g. the aortic annulus is achieved.

The sealing elements arranged and attached to the valve element, thus, and in other words, form intermittent/interrupted ring structures with gaps, so that less material at one level (in the circumferential and longitudinal direction) is provided at the valve element, the fact of which facilitates loading of the prosthesis onto, e.g., a deployment catheter. The distribution of the sealing elements on the valve elements, thus, forms a labyrinth-like pattern.

According to a preferred embodiment, the sealing elements of the prosthetic heart valve according to the invention have the form of stripes and have a length and a width, and the sealing elements extend, relative to their width, on the outer surface of the valve element in a direction P that is perpendicular to the longitudinal axis of the valve element.

In this embodiment, and in other words, the sealing elements formed as stripes, which preferably-before having them attached to the valve to form the lip element—have a substantially rectangular, elliptical or circular form, each extend over a part of the circumference of the prosthetic heart valve, while the sealing elements having a lip-shaped form do not touch each other.

In this context, the term "stripes" or "stripe" or piece of "stripe" means any substantially rectangular element, whose one side, i.e. the "length" is longer than the other side, i.e. the width.

According to a preferred embodiment of the prosthetic heart valve according to the invention, the sealing elements are—relative to the circumference of the valve element-spaced apart from one another at regular or irregular distances.

In this regard, "spaced apart from one another at regular or irregular distances relative to the circumference of the valve element" means that on the one hand, the sealing elements are distributed over the circumference of the valve element such, that the distance between the plurality of sealing elements arranged and attached on the valve element can be either the same (=regular) or different (=irregular). Also, the sealing elements can be arranged-spaced apart from one another-on the same circumferential line in a regular or irregular distance, and/or can be offset with respect to one another.

According to a preferred embodiment of the prosthetic heart valve according to the invention, the sealing elements are—relative to the longitudinal axis of the valve element-spaced apart from one another at a regular or irregular distance.

In this regard, "spaced apart from one another at regular or irregular distances relative to the longitudinal axis of the valve element" means that on the one hand, the sealing elements are attached and distributed over the valve element such, that the distance between the plurality of sealing elements arranged and attached on the valve element can be either the same (=regular) or different (=irregular) when referring to the longitudinal axis of the valve element. Also, the sealing elements can be arranged—spaced apart from one another-on the same line with respect to the longitudinal axis in a regular or irregular distance, and/or can be offset with respect to one another.

According to an embodiment of the present invention, the sealing elements can be spaced apart from one another at regular or irregular distances relative to the circumference, and/or the sealing elements can be spaced apart from one another at regular or irregular distances relative to longitudinal axis of the valve element.

According to a preferred embodiment of the prosthetic heart valve according to the invention, at least two of the sealing elements have the same or different lengths and/or widths.

According to the invention, the sealing elements do not necessarily have to have the same shape and/or dimensions. Accordingly, each of the sealing elements can have a shape that is different to the others, as long as they fulfill the forming of lip-shaped elements, and/or their shapes can have dimensions that are different from one another.

According to a preferred embodiment, at least two sealing elements have the same shape and/or dimension (length, width). The at least two sealing elements having the same shape and/or dimension can be arranged in the circumferential direction, or with respect to the longitudinal axis of the valve element.

Further, according to a preferred embodiment of the prosthetic heart valve according to the invention, all sealing elements that are arranged in the same line with respect to the circumference of the valve element and/or all sealing elements that are arranged in the same line with respect to the longitudinal axis of the valve element have the same shape and/or dimension.

As mentioned before, according to a preferred embodiment of the prosthetic heart valve according to the invention, the sealing elements have a substantially rectangular shape, having a length in the range of between 1 to 80 mm preferably between 1 to 20 mm and having a width in the range of between 1 to 20 mm preferably between 1 to 10 mm.

According to another embodiment, the sealing elements have a substantially elliptical or circular shape, with a diameter in the range of between 1 mm and 80 mmm preferably between 1-20 mm.

According to a preferred embodiment of the prosthetic heart valve according to the invention, the sealing elements are lengthwise attached onto the outer surface of the valve element relative to the circumference of the valve element.

The attachment of the sealing elements to the outer surface of the valve element can be effected by any suitable attachment means, e.g. by sewing, stitching, gluing, stapling or otherwise.

Accordingly, and according to a preferred embodiment of the prosthetic heart valve according to the invention, the plurality of sealing elements is stitched to the outer surface of the valve element.

According to a preferred embodiment of the prosthetic heart valve according to the invention, the lip-shaped elements formed by the sealing elements at least partially protrude through the generally tubular stent support, such, that the sealing elements, in the implanted state of the prosthetic heart valve, touch the surrounding valve tissue, thus sealing the valve and preventing paravalvular leakage.

According to a preferred embodiment of the prosthetic heart valve according to the invention, the stent support comprises a plurality of adjacent rows of interconnected, substantially diamond-shaped open cell structures, and wherein, in the expanded state, the lip-shaped elements at least partially protrude through the cell structures.

In this embodiment, the lip-shaped elements, at least partially protrude through the cell structures of the stent support and contact and seal the surrounding valve tissue.

According to a preferred embodiment of the prosthetic heart valve according to the invention, the prosthetic heart valve comprises between 2 and 20 sealing elements, preferably between 2 and 15, more preferably between 2 and 10 sealing elements.

Further, the prosthetic heart valve, according to a preferred embodiment, comprises between 2 to 5 sealing elements in a circumferential line, and/or 2 to 4 sealing elements referring to a line of the longitudinal axis.

According to a preferred embodiment of the prosthetic heart valve according to the invention, the plurality of sealing elements is arranged on outer surface of the valve element such, that rows of non-tangent lip-shaped elements are formed, each row comprising sealing elements spaced apart from one another relative to circumference of the valve element at a distance R, and wherein the rows are spaced apart from one another relative to the longitudinal axis of the valve element at a distance S.

According to a preferred embodiment of the prosthetic heart valve according to the invention, the prosthetic heart valve comprises a first row and a second row of sealing elements arranged on the outer surface of the valve element, the first and second row each comprising sealing elements spaced apart from one another relative to the circumference of the valve element at a distance R, wherein the sealing elements of the first row are, relative to the longitudinal axis of the valve element, arranged offset relative to the sealing elements of the second row.

According to a preferred embodiment of the prosthetic heart valve according to the invention, the prosthetic heart valve comprises a first, a second, and a third row of sealing elements arranged on the outer surface of the valve element, the first, the second, and the third row each comprising sealing elements spaced apart from one another relative to the circumference of the valve element at a distance A, wherein the sealing elements of the first row are, relative to the longitudinal axis of the valve element, offset to the sealing elements of the second and third row.

In case where the prosthetic heart valve comprises two or more rows of sealing elements, it is noted that the arrangement of the rows on the outer surface of the valve can depend on the very nature of the native valve/tissue that is in need of support or replacement. As such, the rows can be located more in the middle portion of the prosthetic heart valve or more towards the proximal end.

According to a preferred embodiment of the prosthetic heart valve according to the invention, the sealing elements comprise or consist of a natural tissue or biocompatible synthetic material.

Preferably, the natural tissue or material is pericardial tissue, and the biocompatible synthetic material is selected from polyester, polyurethane, polystyrene, polytetrafluorethylene, ultra-high-molecular-weight polyethylene (UHMPE), and mixtures thereof.

According to a preferred embodiment of the prosthetic heart valve of the invention, the valve element, comprising a valve body skirt and leaflets, can comprise a material that is selected from porcine, bovine, equine or other mammalian tissue, such as pericardial tissue, and are sewn, welded, molded or glued together so as to efficiently distribute forces along the leaflets and to the stent support. Alternatively, the valve body may comprise a synthetic or polymeric material.

According to a preferred embodiment of the prosthetic heart valve of the invention, the prosthetic heart valve can be used for treating, replacing or supporting a native heart valve that is selected from a mitral valve, tricuspid valve, pulmonary valve and aortic valve.

It is understood that the features described hereinabove and those still to be described below fall within the scope of the present invention not only in the respectively specified combinations, but also in different combinations or on their own, such, that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Preferred embodiments are shown in the Figures and are described in further detail herein below.

EMBODIMENTS

The accompanying drawings, which are incorporated herein and form a part of the specification, further serve to explain the principles of the invention and to enable a person skilled in the pertinent art to make and use the invention. The drawings are not to scale.

Specific embodiments of the present invention are now described with reference to the figures, wherein like reference numbers indicate identical or functionally similar elements. If utilized herein, the terms "distal" or "distally" refer to a position or in a direction away from the heart and the terms "proximal" and "proximally" refer to a position near or in a direction toward the heart. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1A:
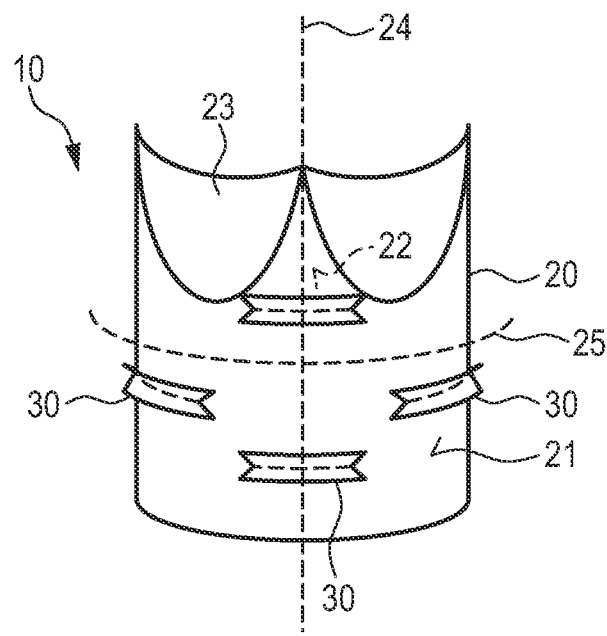
FIGS. 1A and 1B are illustrations of a front view of a portion of the valve element of an exemplary prosthetic heart valve (1A), with (1B) showing a somewhat enlarged side view and displaying one sealing element.

In FIG. 1, a valve element 20 of a prosthetic heart valve 10 is shown, having an outer surface 21, an inner surface 22, leaflets, a longitudinal axis 24 and a circumference 25, which are, respectively, indicated by dotted lines.

As shown in FIG. 1, the valve element 20 comprises sealing elements 30 which are attached to the outer surface 21 of the valve element 20. In the embodiment shown here, the sealing elements 30 are arranged such, that the sealing elements are distributed on the outer surface 21 of the valve element 20, with two sealing elements 30 being spaced apart and arranged in the same line of the longitudinal axis 24, and with two sealing elements 30 being spaced apart and arranged in the same line in the circumference or circumferential direction 25. Also, as can be seen from FIG. 1, the sealing elements 30 arranged in the longitudinal axis 24 and the sealing elements 30 arranged in the circumference are spaced apart.

In other words, the sealing elements 30 form ring-like rows in the circumference 25, with gaps between one another and being offset with respect to the sealing elements 30 of a neighboring/following row.

Figure 1B:
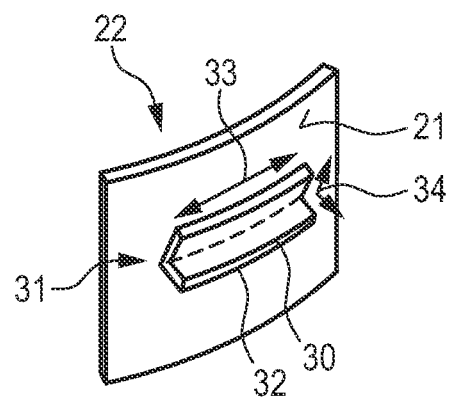

As can be seen in more detail in FIG. 1B, in the embodiment shown in this figure, the sealing elements 30 have the form of pieces of longitudinal stripes 32, having a length 33 and a width 34.

As can be further taken from FIG. 1, the stripes 32 are folded in about their middle along their length 33, to from a lip-shaped element 31. The lip-shaped element 31, thus, comprises two moveable strip-portions, while being attached via the common/joined portion to the valve element. In the embodiment shown in FIG. 1, the sealing elements 30 are sewn onto the outer surface 21 of the valve element 20.

It is noted that it is not mandatory to fold the sealing elements in exactly their middle; other folding techniques and dimensions can be applied, as long as two adjacent flaps are formed which are attached to the valve element 20 via a joint area or line. The ends of the lips or flaps are freely moveable and projected through a stent support in the state where the valve element 20 is mounted on a stent support.

Figure 2:
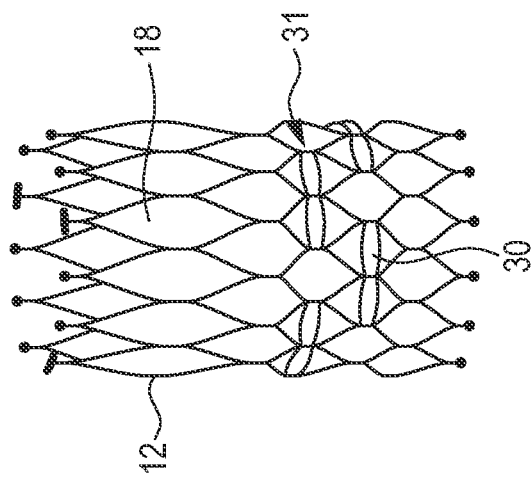
FIG. 2 is an illustration of an exemplary prosthetic heart valve, with the valve element mounted on the inner surface of the stent support, with the embodiments shown on the left and in the middle having three rows of sealing elements, and with the embodiment shown on the right having two rows of sealing elements.
Figure 2:
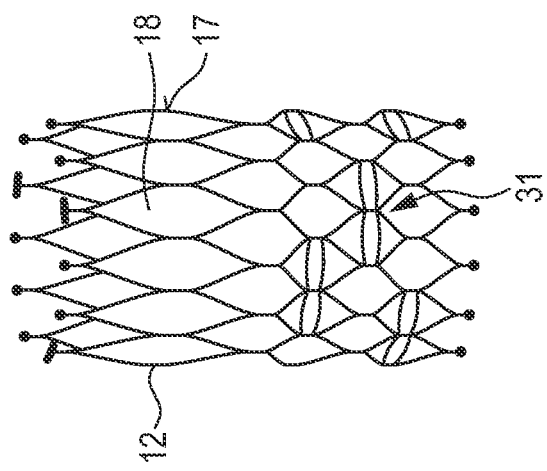
Figure 2:
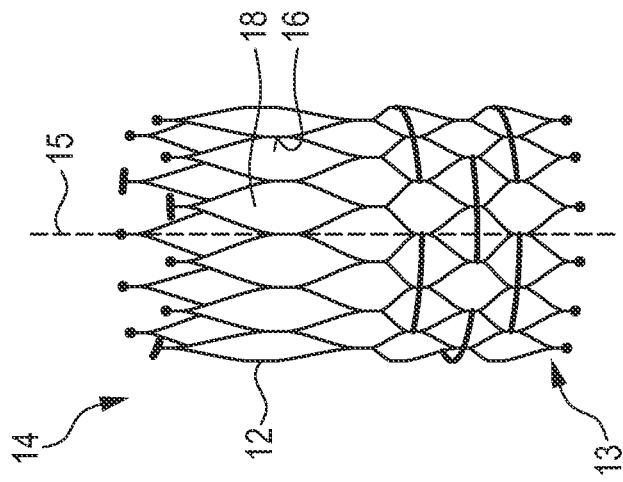

This can be seen more clearly in FIG. 2, where the valve element 20 is mounted on an inner surface 16 of a stent support 12 of an exemplary embodiment of the prosthetic heart valve according to the invention. In FIG. 2 however, for the sake of clarity, the valve element 20 is not depicted, but only the sealing elements 30 (which are attached to the valve element 20), which project through the stent support 12, or rather through the openings in the meshes of the stent-support 12.

The stent support 12 has a generally tubular form and has a proximal end 13, a distal end 14 and a longitudinal axis 15, extending from the proximal end 13 to the distal end 14, as indicated by the dotted line in FIG. 2, in the embodiments shown at the very left. The stent support 12 is expandable and has-due to its generally tubular form—an inner surface 16 and an outer surface 17. The outer surface, in the state where the prosthetic heart valve is deployed in the heart of the patient to be treated, contacts the surrounding native walls/tissues; the inner surface 116 carries the valve element 20, since the valve element 20 is mounted thereon, thus providing for a blood lumen within the stent-support 12.

As can be seen in FIG. 2, the stent support 12 is comprised of intersecting wires, which are preferably made of nitinol, the intersecting wires forming cell structures 18, which are generally diamond-shaped.

The lip-shaped elements 31, formed through the sealing elements 20, partially protrude through the cell-structures 18. "Partially" in this connection, and throughout the application, means that the lip-shaped elements 31 do not protrude or rather cannot protrude, where their protrusion is prevented by the structures of the stent-support 12, i.e. by the wires or wire-intersections.

Figure 3:
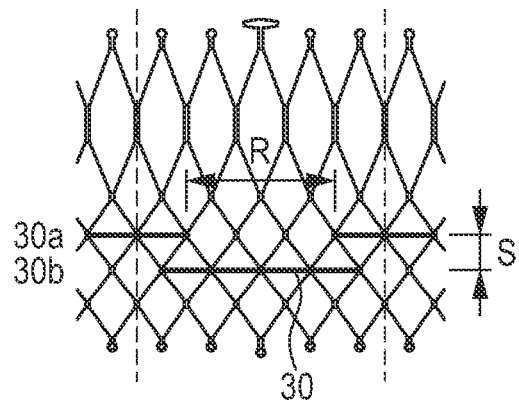
FIG. 3 is a schematic illustration of different embodiments of a prosthetic heart valve according to the invention, with different patterns of the distribution of the sealing elements over the valve elements.
Figure 3:
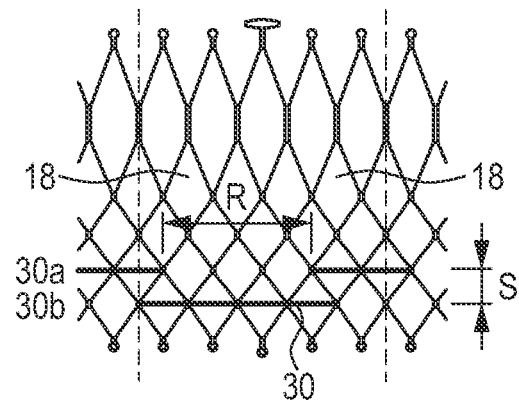
Figure 3:
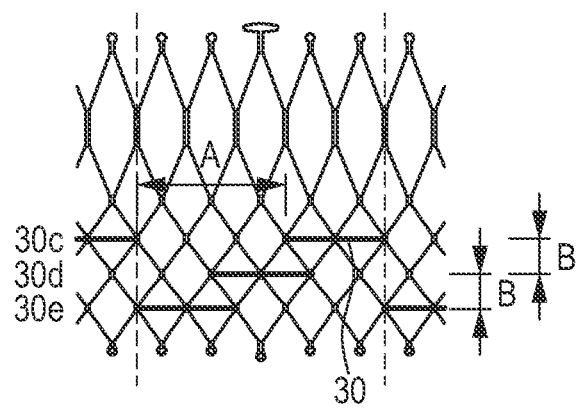
Figure 3:
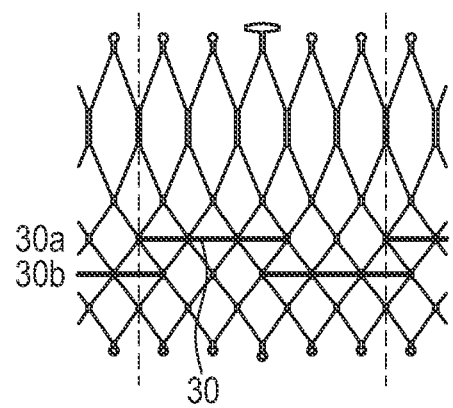

FIG. 3 shows a schematic illustration of exemplary embodiments of the prosthetic heart valve 10 of the invention, and specifically depicts exemplary patters for the distribution of the sealing elements 30 over the valve element 20. As for FIG. 1, the valve element 20, having attached thereto the sealing elements 30 on the outer surface 21, is not depicted for the sake of clarity of the Figure. Rather, the stent support 12 is shown, and the arrangement of the sealing elements 30 relative thereto.

In the embodiments shown upper left, the prosthetic heart valve 10 comprises two rows of sealing elements 30, a first row 30a and a second row 30b, which second row 30b, is arranged in the proximal direction (i.e. towards the proximal end 13 of the stent support 12) from the first row 30a. The sealing elements 30 of the first row 30a are, relative to the circumference 25 of the valve element 20, spaced apart from one another at a distance R. The sealing elements 30 of the second row 30b are arranged offset to the sealing element 30 of the first row 30a, and thus, are not arranged in direct line with the sealing elements of the first row 30a, when seen in the direction of/relative to the longitudinal axis 24. Further, the sealing elements 30 of the second row 30b are spaced apart from the sealing elements 30 of the first row 30 at a distance 2, measured or seen in the direction of the longitudinal axis 24.

In the embodiment shown upper right, there are also two rows of sealing elements, with the distance R of the sealing elements 30 relative to the circumference 25 being smaller than that of the sealing elements 30 in the upper left embodiment. Also, in the upper right embodiment, the two rows 30a and 30b are arranged on the valve element 20 at a position that is nearer to the proximal end 13.

In the embodiment shown in the lower left, three rows 30c, 30d, 30e of sealing elements 30 are provided, with the sealing elements 30 of row 30c, 30d, 30e being spaced apart at a distance A relative to the circumference, respectively. Row 30d is arranged at a distance and following row 30c towards the proximal end 13 of the stent support 12, and row 30e is arranged at a distance and following row 30d towards the proximal end 13. As for the embodiments shown in the upper half of FIG. 3, the sealing elements 30 of rows 30c, 30d, 30e are offset with respect to the sealing elements 30 of the respectively following or neighboring row. In the embodiment shown in FIG. 3, the sealing elements 30, when seen with respect to the longitudinal axis, are only overlapping with their respective ends, and are spaced apart in the direction of the longitudinal axis at a distance S.

However, it is noted, that according to the invention, it is not mandatory that in the direction of the longitudinal axis, the sealing elements do overlap with their ends. In other embodiments, not even the very ends of the sealing elements do overlap with sealing elements of a row following another row in the direction towards the proximal end of the stent support.

In the embodiment shown at the lower right, also two rows 30a, 30b of sealing elements 30 are provided, again with a different pattern as compared to the other embodiments.

It is noted for all embodiments presently shown and disclosed that the sealing elements 30 can be arranged on the surface of the valve element 20 such, that the line of attachment of the sealing elements 30 is in alignment with the crossings of the wires forming the stent support. However, this alignment is not mandatory, and a more arbitrarily distribution of the sealing elements 30 can be provided for.

The foregoing and other features and advantages of the invention will be apparent from the following description of embodiments hereof as illustrated in the accompanying drawings.

The invention claimed is:

1. Prosthetic heart valve configured for supporting or replacing a non- or malfunctioning native heart valve, the prosthetic heart valve being expandable from a compressed state to an expanded state, and comprising:
   an expandable generally tubular stent support, and having a proximal end, a distal end, and a longitudinal axis extending from the proximal end to the distal end, wherein the tubular stent support has an inner surface and an outer surface,
   a valve element, having an outer surface, an inner surface, leaflets, a longitudinal axis and a circumference;
   a plurality of sealing elements, wherein the sealing elements are spaced apart from one another and circumferentially attached to the outer surface of the valve element without being tangent to one another, such, that each of sealing element, in the expanded state, forms a lip-shaped element radially protruding from the outer surface of the valve element,
   wherein the valve element having the sealing elements attached thereon is mounted on the inner surface of the stent support, and
   wherein the sealing elements have the form of stripes and have a length and a width, and wherein the sealing elements extend, relative to their width, on the outer surface of the valve element in a direction P that is perpendicular to the longitudinal axis of the valve element.

2. The prosthetic heart valve of claim 1, wherein the sealing elements, relative to the circumference of the valve element, are spaced apart from one another at regular or irregular distances.

3. The prosthetic heart valve of claim 1, wherein the sealing elements, relative to the longitudinal axis of the valve element, are spaced apart from one another at a regular or irregular distance.

4. The prosthetic heart valve of claim 1, wherein at least two of the sealing elements have the same or different lengths and/or widths.

5. The prosthetic heart valve of claim 1, wherein the sealing elements are lengthwise attached onto the outer surface of the valve element relative to the circumference of the valve element.

6. The prosthetic heart valve of claim 1, wherein the plurality of sealing elements is stitched to the outer surface of the valve element.

7. The prosthetic heart valve of claim 1, wherein the stent support comprises a plurality of adjacent rows of interconnected, substantially diamond-shaped open cell structures, and wherein, in the expanded state, the lip-shaped elements at least partially protrude through the cell structures.

8. The prosthetic heart valve of claim 1, comprising between 2 and 20 sealing elements.

9. The prosthetic heart valve of claim 1, wherein the plurality of sealing elements is arranged on outer surface of the valve element such, that rows of non-tangent lip-shaped elements are formed, each row comprising sealing elements spaced apart from one another relative to circumference of the valve element at a distance R, and wherein the rows are spaced apart from one another relative to the longitudinal axis of the valve element at a distance S.

10. The prosthetic heart valve of claim 1, comprising a first row and a second row of sealing elements arranged on the outer surface of the valve element, the first and second row each comprising sealing elements spaced apart from one another relative to the circumference of the valve element at a distance R, wherein the sealing elements of the first row are, relative to the longitudinal axis of the valve element, arranged offset relative to the sealing elements of the second row.

11. The prosthetic heart valve of claim 1, comprising a first, a second, and a third row of sealing elements arranged on the outer surface of the valve element, the first, the second, and the third row each comprising sealing elements spaced apart from one another relative to the circumference of the valve element at a distance A, wherein the sealing elements of the first row are, relative to the longitudinal axis of the valve element, offset to the sealing elements of the second and third row.

12. The prosthetic heart valve of claim 1, wherein the sealing elements comprise or consist of a natural tissue or biocompatible synthetic material.

13. The prosthetic heart valve of claim 1, wherein the sealing elements comprise or consist of a tissue or material that is selected from pericardial tissue, polyester, polyurethane, polystyrene, polytetrafluorethylene, ultra-high-molecular-weight polyethylene(UHMPE), and mixtures thereof.

* * * * *